(12) United States Patent
Senn-Bilfinger

(10) Patent No.: US 6,384,048 B1
(45) Date of Patent: May 7, 2002

(54) IMIDAZONAPHTHYRIDINES

(75) Inventor: Jörg Senn-Bilfinger, Constance (DE)

(73) Assignee: Byk Gulden Lomberg Chemische Fabrik GmbH, Konstanz (DE)

( * ) Notice: Subject to any disclaimer, the term of this patent is extended or adjusted under 35 U.S.C. 154(b) by 0 days.

(21) Appl. No.: 09/807,970

(22) PCT Filed: Oct. 29, 1999

(86) PCT No.: PCT/EP99/08227

§ 371 Date: Apr. 27, 2001

§ 102(e) Date: Apr. 27, 2001

(87) PCT Pub. No.: WO00/26217

PCT Pub. Date: May 11, 2000

(30) Foreign Application Priority Data

Nov. 3, 1998 (EP) .............................. 98120834

(51) Int. Cl.$^7$ .................. A61K 31/4375; C07D 471/14
(52) U.S. Cl. ......................... 514/293; 546/82
(58) Field of Search ............................. 514/293; 546/82

(56) References Cited

U.S. PATENT DOCUMENTS

| | | | |
|---|---|---|---|
| 4,468,400 A | 8/1984 | Gold et al. | 424/256 |
| 6,160,119 A | 12/2000 | Senn-Bilfinger | |
| 6,197,783 B1 * | 3/2001 | Senn-Belfinger et al. | 514/293 |

FOREIGN PATENT DOCUMENTS

| | | |
|---|---|---|
| EP | 0 235 525 | 9/1987 |
| WO | 98/42707 | 10/1998 |

OTHER PUBLICATIONS

U.S. application No. 09/582,212, Senn–Bilfinger.

* cited by examiner

Primary Examiner—Charanjit S. Aulakh
(74) Attorney, Agent, or Firm—Jacobson Holman, PLLC

(57) ABSTRACT

Tetrahydropyrido compounds of formula (I)

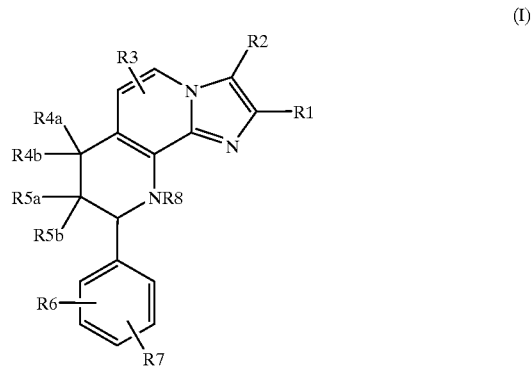

in which the substituents have the meanings mentioned in the description, are suitable for the prevention or treatment of gastrointestinal diseases.

11 Claims, No Drawings

IMIDAZONAPHTHYRIDINES

This application is a 371 of PCT/EP99/08227 filed Oct. 29, 1999, now WO 00/28217 May 11, 2000.

FIELD OF APPLICATION OF THE INVENTION

The invention relates to novel compounds which are used in the pharmaceuticals industry as active compounds for preparing medicaments.

KNOWN TECHNICAL BACKGROUND

U.S. Pat. No. 4,468,400 describes tricyclic imidazo[1,2-a]pyridines having different ring systems fused to the imidazopyridine skeleton, which compounds are said to be suitable for treating peptic ulcer disorders. The International Patent Application WO98/42707 discloses tetrahydroimidazonaphthyridines having a very particular substitution pattern, which compounds are likewise said to be suitable for treating gastrointestinal disorders.

DESCRIPTION OF THE INVENTION

The invention provides compounds of the formula I

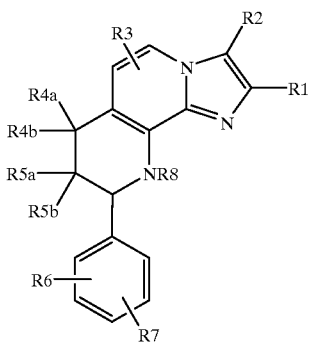

(I)

in which
R1 is 1–4C-alkyl,
R2 is 1–4C-alkyl or hydroxy-1–4C-alkyl,
R3 is hydrogen or halogen,
one of the substituents R4a and R4b is hydrogen and the other is hydrogen, hydroxyl, 1–4C-alkoxy, 1–4C-alkoxy-1–4C-alkoxy, 1–4C-alkylcarbonyloxy or the radical R4', or R4a and R4b together are O (oxygen), where
R4' is
—O—(CH$_2$)$_m$S(O)$_n$—R9,
—S(O)$_r$—(CH$_2$)$_m$—OH,
—S(O)$_n$—(CH$_2$)$_m$—O—R9,
—S(O)$_n$—(CH$_2$)$_m$—S(O)$_p$—R9,
—O-alk1-S(O)$_n$—R9,
—S(O)$_n$—R9,
—S(O)$_n$-alk1-OH,
—S(O),-alk1-O—R9 or
—S(O),-alk1-S(O)$_p$—R9,
in which
R9 is 1–7C-alkyl, halo-1–4C-alkyl, hydroxy-1–4C-alkyl, 1–4C-alkoxy-1–4C-alkyl, carboxy-1–4C-alkyl, 1–4C-alkoxycarbonyl-1–4C-alkyl or di-1–4C-alkylamino-1–4C-alkyl, Ar or Ar-1–4C-alkyl, where Ar is phenyl or substituted phenyl having one, two or three identical or different substituents selected from the group consisting of 1–4C-alkyl, 1–4C-alkoxy, 1–4C-alkylcarbonyl, 1–4C-alkoxycarbonyl, halogen, trifluoromethyl, difluoromethoxy, trifluoromethoxy, amino, 1–4C-alkoxycarbonylamino, 1–4C-alkoxy-1–4C-alkoxycarbonylamino and nitro,
alk1 is 1–4C-alkyl-, hydroxyl-, oxo-, carboxyl-, halogen-, amino-, 1–4C-alkoxycarbonylamino- or phenyl-substituted 2–7C-alkylene or 3–4C-alkenylene,
m is an integer from 2 to 7,
n is the number 0, 1 or 2 and
p is the number 0, 1 or 2,
one of the substituents R5a and R5b is hydrogen and the other is hydrogen, hydroxyl, 1–4C-alkoxy, 1–4C-alkoxy-1–4C-alkoxy, 1–4C-alkylcarbonyloxy or the radical R5', or R5a and R5b together are O (oxygen), where
R5' is
—O—(CH$_2$)$_q$—S(O)$_t$—R10,
—S(O)$_r$(CH$_2$)$_q$—OH,
—S(O)$_r$(CH$_2$)$_q$—O—R10,
—S(O)$_r$(CH$_2$)$_q$—S(O)$_t$—R10,
—O-alk2-S(O)$_t$—R10,
—S(O)$_t$—R10,
—S(O)$_r$-alk2-OH,
—S(O)$_r$-alk2-O—R10 or
—S(O)$_r$-alk2-S(O)$_t$—R10,
in which
R10 is 1–7C-alkyl, halo-1–4C-alkyl, hydroxy-1–4C-alkyl, 1–4C-alkoxy-1–4C-alkyl, carboxy-1–4C-alkyl, 1–4C-alkoxycarbonyl-1–4C-alkyl or di-1–4C-alkylamino-1–4C-alkyl, Ar or Ar-1–4C-alkyl, where Ar is phenyl or substituted phenyl having one, two or three identical or different substituents selected from the group consisting of 1–4C-alkyl, 1–4C-alkoxy, 1–4C-alkylcarbonyl, 1–4C-alkoxycarbonyl, halogen, trifluoromethyl, difluoromethoxy, trifluoromethoxy, amino, 1–4C-alkoxycarbonylamino, 1–4C-alkoxy-1–4C-alkoxycarbonylamino and nitro,
alk2 is 1–4C-alkyl-, hydroxyl-, oxo-, carboxyl-, halogen-, amino-, 1–4C-alkoxycarbonylamino- or phenyl-substituted 2–7C-alkylene or 3–4C-alkenylene,
q is an integer from 2 to 7,
r is the number 0, 1 or 2 and
t is the number 0, 1 or 2,
R6 is hydrogen, halogen, 1–4C-alkyl, 1–4C-alkoxy, 1–4C-alkoxycarbonylamino, 1–4C-alkoxy-1–4C-alkoxycarbonylamino or trifluoromethyl,
R7 is hydrogen, halogen, 1–4C-alkyl or 1–4C-alkoxy and
R8 is hydrogen or 1–4C-alkyl,
and their salts,
where one of the substituents R4a and R4b has to be R4'and/or one of the substituents R5a and R5b has to be R5'.

1–4C-Alkyl represents straight-chain or branched alkyl radicals having 1 to 4 carbon atoms. Examples which may be mentioned are the butyl, isobutyl, sec-butyl, tert-butyl, propyl, isopropyl, ethyl and methyl radicals.

Hydroxy-1–4C-alkyl represents the abovementioned 1–4C-alkyl radicals, substituted by a hydroxyl group. Examples which may be mentioned are the hydroxymethyl, the 2-hydroxyethyl and the 3-hydroxypropyl radicals.

For the purpose of the invention, halogen is bromine, chlorine and fluorine.

1–4C-Alkoxy represents radicals which, in addition to the oxygen atom, contain a straight-chain or branched alkyl radical having 1 to 4 carbon atoms. Examples which may be mentioned are the butoxy, isobutoxy, sec-butoxy, tert-butoxy, propoxy, isopropoxy and preferably the ethoxy and methoxy radicals.

1–4C-Alkoxy-1–4C-alkoxy represents one of the abovementioned 1–4C-alkoxy radicals which is substituted by a further 1–4C-alkoxy radical. Examples which may be mentioned are the radicals 2-(methoxy)ethoxy($CH_3$—O—$CH_2$—$CH_2$—O—) and 2-(ethoxy)-ethoxy($CH_2$—$CH_2$—O—$CH_2$—$CH_2$—O—).

1–4C-Alkylcarbonyl represents a radical which, in addition to the carbonyl group, contains one of the abovementioned 1–4C-alkyl radicals. An example which may be mentioned is the acetyl radical.

1—4C-Alkylcarbonyloxy represents a carbonyloxy group to which is attached one of the abovementioned 1–4C-alkyl radicals. An example which may be mentioned is the acetoxy radical ($CH_3CO$—O—).

1–7C-Alkyl represents straight-chain or branched alkyl radicals having 1 to 7 carbon atoms. Examples which may be mentioned are the heptyl, isoheptyl (5-methylhexyl), hexyl, isohexyl(4-methylpentyl), neohexyl(3,3-dimethylbutyl), pentyl, isopentyl(3-methylbutyl), neopentyl (2,2-dimethylpropyl), butyl, iso-butyl, sec-butyl, tert-butyl, propyl, isopropyl, ethyl and methyl radicals.

Halo-1–4C-alkyl represents one of the abovementioned 1–4C-alkyl radicals which is substituted by one of the abovementioned halogen atoms. An example which may be mentioned is the 3-chloropropyl radical.

1–4C-Alkoxy-1–4C-alkyl represents one of the abovementioned 1–4C-alkyl radicals which is substituted by one of the abovementioned 1–4C-alkoxy radicals. Examples which may be mentioned are the methoxymethyl, the methoxyethyl and the butoxyethyl radicals.

Carboxy-1–4alkyl represents, for example, the carboxymethyl (—$CH_2COOH$) or the carboxyethyl (—$CH_2CH_2COOH$) radicals.

1–4C-Alkoxycarbonyl represents a carbonyl group to which is attached one of the abovementioned 1–4C-alkoxy radicals. Examples which may be mentioned are the methoxycarbonyl ($CH_3O$—C(O)—) and the ethoxycarbonyl ($CH_3CH_2O$—C(O)—) radicals.

1–4C-Alkoxycarbonyl-1–4C-alkyl represents one of the abovementioned 1–4C-alkyl radicals which is substituted by one of the abovementioned 1–4C-alkoxycarbonyl radicals. An example which may be mentioned is the ethoxycarbonylmethyl radical ($CH_3CH_2OC(O)CH_2$—).

Di-1–4C-alkylamino represents an amino radical which is substituted by two of the abovementioned 1–4C-alkyl radicals, which may be identical or different. Examples which may be mentioned are the dimethylamino, the diethylamino and the diisopropylamino radicals.

Di-1–4C-alkylamino-1–4C-alkyl represents one of the abovementioned 1–4C-alkyl radicals which is substituted by one of the abovementioned di-1–4C-alkylamino radicals. Examples which may be mentioned are the dimethylaminomethyl, the dimethylaminoethyl and the diethylaminoethyl radicals.

Ar-1–4C-alkyl represents one of the abovementioned 1–4C-alkyl radicals which is substituted by Ar, where Ar is as defined above. Examples which may be mentioned are the phenethyl and the benzyl radicals.

1–4C-Alkoxycarbonylamino represents an amino radical which is substituted by one of the abovementioned 1–4C-alkoxycarbonyl radicals. Examples which may be mentioned are the ethoxycarbonylamino and the methoxycarbonylamino radicals.

1–4C-Alkoxy-1–4C-alkoxycarbonyl represents a carbonyl group to which is attached one of the abovementioned 1–4C-alkoxy-1–4C-alkoxy radicals. Examples which may be mentioned are the 2-(methoxy)ethoxycarbonyl ($CH_3$—O—$CH_2CH_2$—CO—) and the 2-(ethoxy)ethoxycarbonyl ($CH_3CH_2$—O—$CH_2CH_2$—O—CO—) radicals.

1–4C-Alkoxy-1–4C-alkoxycarbonylamino represents an amino radical which is substituted by one of the abovementioned 1–4C-alkoxy-1–4C-alkoxycarbonyl radicals. Examples which may be mentioned are the 2-(methoxy)-ethoxycarbonylamino and the 2-(ethoxy) ethoxycarbonylamino radicals.

1–7C-Alkylene represents straight-chain or branched 1–7C-alkene radicals, for example the methylene (—$CH_2$—), ethylene (—$CH_2$—$CH_2$—), tetramethylene (—$CH_2$—$CH_2$—$CH_2$—), tetramethylene (—$CH_2$—$CH_2$—$CH_2$—$CH_2$—), 1,2-dimethylethylene [—CH($CH_3$)—CH($CH_3$)—], 1,1-dimethylethylene [—C($CH_3$)$_2$—$CH_2$—], 2,2-dimethylethylene [—$CH_2$—C($CH_3$)$_2$—], 1,1-isopropylidene [—C($CH_3$)$_2$—], 1-methylethylene [—CH($CH_3$)—$CH_2$—], pentamethylene [—$CH_2$—$CH_2$—$CH_2$—$CH_2$—$CH_2$—), hexamethylene (—$CH_2$—$CH_2$—$CH_2$—$CH_2$—$CH_2$—$CH_2$—) and the heptamethylene (—$CH_2$—$CH_2$—$CH_2$—$CH_2$—$CH_2$—$CH_2$—$CH_2$—) radicals.

3–4C-Alkenylene represents straight-chain 3–4C-alkenylene radicals, for example the 1-propenylene, the 2-propenylene, the 2-butenylene and the 3-butenylene radicals.

Suitable salts of compounds of the formula I are—depending on the substitution—in particular all acid addition salts. Particular mention may be made of the pharmacologically acceptable salts of the inorganic and organic acids customarily used in pharmacy. Those suitable are water-soluble and water-insoluble acid addition salts with acids such as, for example, hydrochloric acid, hydrobromic acid, phosphoric acid, nitric acid, sulfuric acid, acetic acid, citric acid, D-gluconic acid, benzoic acid, 2-(4-hydroxybenzoyl) benzoic acid, butyric acid, sulfosalicylic acid, maleic acid, lauric acid, malic acid, fumaric acid, succinic acid, oxalic acid, tartaric acid, embonic acid, stearic acid, toluenesulfonic acid, methanesulfonic acid or 3-hydroxy-2-naphthoic acid, where the acids are employed in the salt preparation in an equimolar ratio or a ratio differing therefrom, depending on whether the acid is a mono- or polybasic acid and on which salt is desired.

Pharmacologically unacceptable salts, which can be initially obtained, for example, as process products in the preparation of the compounds according to the invention on an industrial scale, are converted into pharmacologically acceptable salts by processes known to the person skilled in the art.

It is known to the person skilled in the art that the compounds according to the invention and their salts can, for example when they are isolated in crystalline form, comprise varying amounts of solvents. The invention therefore also embraces all solvates and, in particular, all hydrates of the compounds of the formula I, and all solvates and, in particular, all hydrates of the salts of the compounds of the formula I.

The compounds of the formula I have at least three chiral centers. The invention provides all eight feasible stereoisomers in any mixing ratio, including the pure enantiomers which are the preferred subject matter of the invention.

An exemplary preferred radical R1 is the methyl radical.

Exemplary preferred radicals R2 are the methyl and the hydroxymethyl radicals.

In the context of the present invention, R3 is preferably hydrogen.

Exemplary radicals R9 or R10 which may be mentioned are: methyl, ethyl, propyl, isopropyl, butyl, isobutyl, pentyl, difluoromethyl, 2,2,2-trifluoroethyl, 2-hydroxy-ethyl, 3-hydroxypropyl, methoxymethyl, methoxyethyl, ethoxymethyl, ethoxyethyl, carboxymethyl, carboxyethyl, carboxypropyl, methoxycarbonylmethyl, dimethylaminoethyl, diethylaminoethyl, phenyl, benzyl, 4-chlorophenyl, 4-aminophenyl, 4-chlorobenzyl, 4-difluoromethoxyphenyl, 4-trifluoromethoxyphenyl, 4-methylbenzyl, 3-methylbenzyl, 2,4-diaminophenyl, 2-methyl-4-tert-butylphenyl, 2-nitro-4-acetylphenyl, 4-fluorobenzyl, 4-nitrophenyl, 3-nitrophenyl, 3-aminophenyl, 2-methoxycarbonylamino-6-methylphenyl, 2-methoxyethoxycarbonylamino-6-methylphenyl, 2-methoxycarbonylamino-6-methylbenzyl and 2-methoxyethoxycarbonylamino-6-methylbenzyl.

Exemplary alkylene and alkenylene groups alk1 and alk2, respectively, which may be mentioned are: 1-methylethylene, 2-methylethylene, 1-phenylethylene, 2-phenylethylene, 1-propylpropylene, 3-propylpropylene, 2-aminopropylene, 2-tert-butyloxycarbonylaminopropylene, 2-hydroxypropylene, 2-oxopropylene, 2-carboxypropylene, 1-acetyl-1,2-dimethylethylene, 2-acetyl-1,2-dimethylethylene, 1,1-dimethyl-2-oxoethylene, 1-oxo-2,2-dimethylethylene, 1,3-dioxobutylene, 2,4-dioxobutylene, 1,2-dioxopropylene, 2,3-dioxopropylene, prop-1-enylene, prop-2-enylene, but-1-enylene, but-2-enylene, but-3-enylene, but-4-enylene, buta-1,3-dienylene, buta-2,4-dienylene, 1-oxo-but-2-enylene, 4-oxo-but-2-enylene, 1-oxo-2,2-difluoroethylene, 2-oxo-1,1-difluoroethylene, 1-oxopropylene, 3-oxopropylene, 1-carboxyethylene and 2-carboxyethylene.

Compounds which may be mentioned are those of the formula I in which

R1 is 1–4C-alkyl,
R2 is 1–4C-alkyl or hydroxy-1–4C-alkyl,
R3 is hydrogen,
one of the substituents R4a and R4b is hydrogen and the other is hydrogen, hydroxyl, 1–4C-alkoxy, 1–4C-alkoxy-1–4C-alkoxy or the radical R4',
where
R4' is
—O—(CH$_2$)$_m$—S(O)$_n$—R9,
—S(O)$_n$—(CH$_2$)$_m$—OH,
—S(O)$_n$—(CH$_2$)$_m$—O—R9,
—S(O)$_n$—(CH$_2$)$_m$—S(O)$_p$—R9 or
—S(O)$_n$—R9,
in which
R9 is 1–7C-alkyl, halo-1–4C-alkyl, hydroxy-1–4C-alkyl or 1–4C-alkoxy-1–4C-alkyl,
m is an integer from 2 to 7,
n is the number 0, 1 or 2 and
p is the number 0, 1 or 2,
one of the substituents R5a and R5b is hydrogen and the other is hydrogen, hydroxyl, 1–4C-alkoxy, 1–4C-alkoxy-1–4C-alkoxy or the radical R5',
where
R5' is
—O—(CH$_2$)$_q$—S(O)$_r$R10,
—S(O)$_r$—(CH$_2$)$_q$—OH,
—S(O)$_r$—(CH$_2$)$_q$—O—R10,
—S(O)$_r$—(CH$_2$)$_q$—S(O)$_t$—R10, or
—S(O)$_r$—R10,
in which
R10 is 1–7C-alkyl, halo-1–4C-alkyl, hydroxy-1–4C-alkyl or 1–4C-alkoxy-1–4C-alkyl,
q is an integer from 2 to 7,
r is the number 0, 1 or 2 and
t is the number 0, 1 or 2,
R6 is hydrogen, halogen or trifluoromethyl,
R7 is hydrogen or halogen and
R8 is hydrogen,
and their salts,
where one of the substituents R4a and R4b has to be R4' and/or one of the substituents R5a and R5b has to be R5'.

Compounds according to the invention which are to be emphasized are those of the formula I*

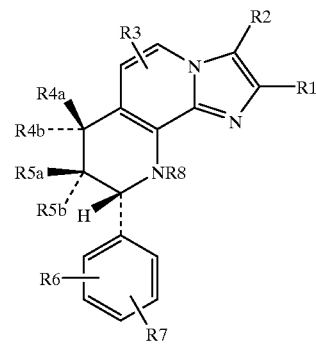

(I*)

in which
R1 is 1–4C-alkyl,
R2 is 1–4C-alkyl or hydroxy-1–4C-alkyl,
R3 is hydrogen,
one of the substituents R4a and R4b is hydrogen and the other is hydrogen, hydroxyl, 1–4C-alkoxy, 1–4C-alkoxy-1–4C-alkoxy or the radical R4',
where
R4' is
—O—(CH$_2$)$_m$—S(O)$_n$—R9,
—S(O)$_n$—(CH$_2$)$_m$—OH,
—S(O)$_n$—(CH$_2$)$_m$—O—R9,
—S(O)$_n$—(CH$_2$)$_m$—S(O)$_p$—R9 or
—S(O)$_n$—R9,
in which
R9 is 1–7C-alkyl, halo-1–4C-alkyl, hydroxy-1–4C-alkyl or 1–4C-alkoxy-1–4C-alkyl,
m is an integer from 2 to 7,
n is the number 0, 1 or 2 and
p is the number 0, 1 or 2,
one of the substituents R5a and R5b is hydrogen and the other is hydrogen, hydroxyl, 1–4C-alkoxy, 1–4C-alkoxy-1–4C-alkoxy or the radical R5',
where
R5' is
—O—(CH$_2$)$_q$—S(O)$_r$—R10,
—S(O)$_r$—(CH$_2$)$_q$—OH,
—S(O)$_r$—(CH$_2$)$_q$—O—R10,
—S(O)$_r$—(CH$_2$)$_q$—S(O)$_t$R10 or
—S(O)$_r$—R10,
in which
R10 is 1–7C-alkyl, halo-1–4C-alkyl, hydroxy-1–4C-alkyl or 1–4C-alkoxy-1–4C-alkyl,
q is an integer from 2 to 7, r is the number 0, 1 or 2 and t is the number 0, 1 or 2, R6 is hydrogen, halogen or trifluoromethyl, R7 is hydrogen or halogen and R8 is hydrogen, and their salts, where one of the substituents R4a and R4b has to be R4' and/or one of the substituents R5a and R5b has to be R5'.

One embodiment (embodiment a) of the compounds of the formula I* to be emphasized are those in which one of the substituents R4a and R4b is hydrogen and the other is the radical R4' and one of the substituents R5a and R5b is hydrogen and the other is hydroxyl.

A further embodiment (embodiment b) of the compounds of the formula I* to be emphasized are those in which one of the substituents R4a and R4b is hydrogen and the other is the radical R4' and one of the substituents R5a and R5b is hydrogen and the other is 1–4C-alkoxy or 1–4C-alkoxy-1–4C-alkoxy.

A further embodiment (embodiment c) of the compounds of the formula I* to be emphasized are those in which one of the substituents R4a and R4b is hydrogen and the other is the radical R4' and one of the substituents R5a and R5b is hydrogen and the other is the radical R5'.

A further embodiment (embodiment d) of the compounds of the formula I* to be emphasized are those in which one of the substituents R4a and R4b is hydrogen and the other is 1–4C-alkoxy or 1–4C-alkoxy-1–4C-alkoxy and one of the substituents R5a and R5b is hydrogen and the other is the radical R5'.

Compounds I* of the embodiments a, b, c and d which are to be emphasized particularly are those in which R1 is 1–4C-alkyl, R2 is 1–4C-alkyl, R3 is hydrogen, R4' is —O—$(CH_2)_m$—$S(O)_n$—R9, —$S(O)_n$—R9, —$S(O)_n$—$(CH_2)_m$—OH or —$S(O)_n$—$(CH_2)_m$—O—R9, in which R9 is 1–4C-alkyl, R5' is —O—$(CH_2)_q$—$S(O)_r$R10, —$S(O)_r$—R10, —$S(O)_r$—$(CH_2)_q$—OH or —$S(O)_r$—$(CH_2)_q$—O—R10, in which R10 is 1–4C-alkyl, R6 is hydrogen, R7 is hydrogen and R8 is hydrogen, and their salts.

Preferred compounds I* of the embodiment a are those in which

R1 is 1–4C-alkyl,

R2 is 1–4C-alkyl,

R3 is hydrogen, one of the substituents R4a and R4b is hydrogen and the other is R4', where R4' is —O—$(CH_2)_m$—$S(O)_n$—R9, —$S(O)_n$—R9, —$S(O)_n$—$(CH_2)_m$—OH or —$S(O)_n$—$(CH_2)_m$—O—R9, in which R9 is 1–4C-alkyl, m is the number 2 or 3 and n is the number 0, 1 or 2, one of the substituents R5a and R5b is hydrogen and the other is hydroxyl, R6 is hydrogen, R7 is hydrogen and R8 is hydrogen, and their salts.

Preferred compounds I* of the embodiment b are those in which

R1 is 1–4C-alkyl,

R2 is 1–4C-alkyl,

R3 is hydrogen, one of the substituents R4a and R4b is hydrogen and the other is R4', where R4' is —O—$(CH_2)_m$—$S(O)_n$—R9, —$S(O)_n$—R9, —$S(O)_n$—$(CH_2)_m$—OH or —$S(O)_n$—$(CH_2)_m$—O—R9, in which R9 is 1–4C-alkyl, m is the number 2 or 3 and n is the number 0,1 or 2, one of the substituents R5a and R5b is hydrogen and the other is 1–4C-alkoxy or 1–4C-alkoxy-1–4C-alkoxy, R6 is hydrogen, R7 is hydrogen and R8 is hydrogen, and their salts.

Preferred compounds I* of the embodiment c are those in which

R1 is 1–4C-alkyl,

R2 is 1–4C-alkyl,

R3 is hydrogen, one of the substituents R4a and R4b is hydrogen and the other is R4', where R4' is —O—$(CH_2)_m$—$S(O)_n$—R9, —$S(O)_n$—R9, —$S(O)_n$—$(CH_2)_m$—OH or —$S(O)_n$—$(CH_2)_m$—O—R9, in which R9 is 1–4C-alkyl, m is the number 2 or 3 and n is the number 0, 1 or 2, one of the substituents R5a and R5b is hydrogen and the other is R5', where R5' is —O—$(CH_2)_q$—$S(O)_r$—R10, —$S(O)_r$—R10, —$S(O)_r$—$(CH_2)_q$—OH or —$S(O)_r$—$(CH_2)_q$—O—R10, in which R10 is 1–4C-alkyl, q is the number 2 or 3 and r is the number 0,1 or 2, R6 is hydrogen, R7 is hydrogen and R8 is hydrogen, and their salts.

Preferred compounds I* of the embodiment d are those in which
R1 is 1–4C-alkyl,
R2 is 1–4C-alkyl,
R3 is hydrogen,
one of the substituents R4a and R4b is hydrogen and the other is 1–4C-alkoxy or 1–4C-alkoxy-1–4C-alkoxy
one of the substituents R5a and R5b is hydrogen and the other is R5',
where
R5' is
—O—(CH$_2$)$_q$—S(O)$_n$—R10,
—S(O)$_r$—R10,
—S(O)$_r$—(CH$_2$)$_q$—OH or
—S(O)$_r$—(CH$_2$)$_q$—O—R10,
in which R10 is 1–4C-alkyl,
q is the number 2 or 3 and
r is the number 0, 1 or 2,
R6 is hydrogen
R7 is hydrogen and
R8 is hydrogen, Selected preferred compounds I* are those of the embodiments a, b, c and d in which R5b is hydrogen.

Selected particularly preferred compounds I* are those of the embodiments a, b, c and d in which R5b is hydrogen and R4a is hydrogen.

The following preferred compounds according to the invention selected by way of example may be mentioned specifically using formula I* below with the substituent definitions for R4a, R4b and R5a of Table 1 (Tab. 1) below:

TABLE 1

I**

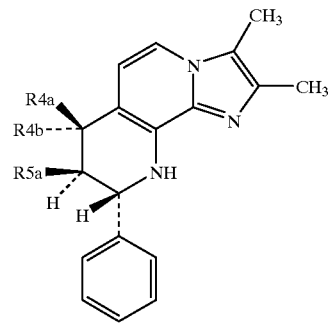

| R4a | R4b | R5a |
|---|---|---|
| H | —OCH$_2$CH$_2$SCH$_3$ | —OH |
| H | —OCH$_2$CH$_2$SOCH$_3$ | —OH |
| H | —OCH$_2$CH$_2$SO$_2$CH$_3$ | —OH |
| H | —SCH$_2$CH$_2$OCH$_3$ | —OH |
| H | —SOCH$_2$CH$_2$OCH$_3$ | —OH |
| H | —SO$_2$CH$_2$CH$_2$OCH$_3$ | —OH |
| H | —SCH$_2$CH$_2$OH | —OH |
| H | —SCH$_3$ | —OH |
| H | —SOCH$_3$ | —OH |
| H | —SO$_2$CH$_3$ | —OH |
| H | —SCH$_2$CH$_3$ | —OH |
| H | —SOCH$_2$CH$_3$ | —OH |
| H | —SO$_2$CH$_2$CH$_3$ | —OH |
| H | —SCH$_2$CH$_2$CH$_3$ | —OH |
| H | —SOCH$_2$CH$_2$CH$_3$ | —OH |
| H | —SO$_2$CH$_2$CH$_2$CH$_3$ | —OH |
| H | —SCH(CH$_3$)$_2$ | —OH |
| H | —SOCH(CH$_3$)$_2$ | —OH |
| H | —SO$_2$CH(CH$_3$)$_2$ | —OH |
| H | —SCH$_2$COOCH$_2$CH$_3$ | —OH |
| H | —SOCH$_2$COOCH$_2$CH$_3$ | —OH |
| H | —SO$_2$CH$_2$COOCH$_2$CH$_3$ | —OH |
| —OCH$_2$CH$_2$SCH$_3$ | H | —OH |
| —OCH$_2$CH$_2$SOCH$_3$ | H | —OH |
| —OCH$_2$CH$_2$SO$_2$CH$_3$ | H | —OH |
| —SCH$_2$CH$_2$OCH$_3$ | H | —OH |
| —SOCH$_2$CH$_2$OCH$_3$ | H | —OH |
| —SO$_2$CH$_2$CH$_2$OCH$_3$ | H | —OH |
| —SCH$_2$CH$_2$OH | H | —OH |
| —SCH$_3$ | H | —OH |
| —SOCH$_3$ | H | —OH |
| —SO$_2$CH$_3$ | H | —OH |
| —SCH$_2$CH$_3$ | H | —OH |
| —SOCH$_2$CH$_3$ | H | —OH |
| —SO$_2$CH$_2$CH$_3$ | H | —OH |
| —SCH$_2$CH$_2$CH$_3$ | H | —OH |
| —SOCH$_3$CH$_2$CH$_3$ | H | —OH |
| —SO$_2$CH$_2$CH$_2$CH$_3$ | H | —OH |

TABLE 1-continued

I**

| R4a | R4b | R5a |
|---|---|---|
| —SCH(CH₃)₂ | H | —OH |
| —SOCH(CH₃)₂ | H | —OH |
| —SO₂CH(CH₃)₂ | H | —OH |
| —SCH₂COOCH₂CH₃ | H | —OH |
| —SOCH₂COOCH₂CH₃ | H | —OH |
| —SO₂CH₂COOCH₂CH₃ | H | —OH |
| H | —OCH₂CH₂SCH₃ | —OCH₃ |
| H | —OCH₂CH₂SOCH₃ | —OCH₃ |
| H | —OCH₂CH₂SO₂CH₃ | —OCH₃ |
| H | —SCH₂CH₂OCH₃ | —OCH₃ |
| H | —SOCH₂CH₂OCH₃ | —OCH₃ |
| H | —SO₂CH₂CH₂OCH₃ | —OCH₃ |
| H | —SCH₂CH₂OH | —OCH₃ |
| H | —SCH₃ | —OCH₃ |
| H | —SOCH₃ | —OCH₃ |
| H | —SO₂CH₃ | —OCH₃ |
| H | —SCH₂CH₃ | —OCH₃ |
| H | —SOCH₂CH₃ | —OCH₃ |
| H | —SO₂CH₂CH₃ | —OCH₃ |
| H | —SCH₂CH₂CH₃ | —OCH₃ |
| H | —SOCH₂CH₂CH₃ | —OCH₃ |
| H | —SO₂CH₂CH₂CH₃ | —OCH₃ |
| H | —SCH(CH₃)₂ | —OCH₃ |
| H | —SOCH(CH₃)₂ | —OCH₃ |
| H | —SO₂CH(CH₃)₂ | —OCH₃ |
| H | —SCH₂COOCH₂CH₃ | —OCH₃ |
| H | —SOCH₂COOCH₂CH₃ | —OCH₃ |
| H | —SO₂CH₂COOCH₂CH₃ | —OCH₃ |
| H | —OCH₂CH₂SCH₃ | —OCH₂CH₂OCH₃ |
| H | —OCH₂CH₂SOCH₃ | —OCH₂CH₂OCH₃ |
| H | —OCH₂CH₂SO₂CH₃ | —OCH₂CH₂OCH₃ |
| H | —SCH₂CH₂OCH₃ | —OCH₂CH₂OCH₃ |
| H | —SOCH₂CH₂OCH₃ | —OCH₂CH₂OCH₃ |
| H | —SO₂CH₂CH₂OCH₃ | —OCH₂CH₂OCH₃ |
| H | —SCH₂CH₂OH | —OCH₂CH₂OCH₃ |
| H | —SCH₃ | —OCH₂CH₂OCH₃ |
| H | —SOCH₃ | —OCH₂CH₂OCH₃ |
| H | —SO₂CH₃ | —OCH₂CH₂OCH₃ |
| H | —SCH₂CH₃ | —OCH₂CH₂OCH₃ |
| H | —SOCH₂CH₃ | —OCH₂CH₂OCH₃ |
| H | —SO₂CH₂CH₃ | —OCH₂CH₂OCH₃ |
| H | —SCH₂CH₂CH₃ | —OCH₂CH₂OCH₃ |
| H | —SOCH₂CH₂CH₃ | —OCH₂CH₂OCH₃ |
| H | —SO₂CH₂CH₂CH₃ | —OCH₂CH₂OCH₃ |
| H | —SCH(CH₃)₂ | —OCH₂CH₂OCH₃ |
| H | —SOCH(CH₃)₂ | —OCH₂CH₂OCH₃ |
| H | —SO₂CH(CH₃)₂ | —OCH₂CH₂OCH₃ |
| H | —SCH₂COOCH₂CH₃ | —OCH₂CH₂OCH₃ |
| H | —SOCH₂COOCH₂CH₃ | —OCH₂CH₂OCH₃ |
| H | —SO₂CH₂COOCH₂CH₃ | —OCH₂CH₂OCH₃ |
| —OCH₂CH₂SCH₃ | H | —OCH₃ |
| —OCH₂CH₂SOCH₃ | H | —OCH₃ |
| —OCH₂CH₂SO₂CH₃ | H | —OCH₃ |
| —SCH₂CH₂OCH₃ | H | —OCH₃ |
| —SOCH₂CH₂OCH₃ | H | —OCH₃ |
| —SO₂CH₂CH₂OCH₃ | H | —OCH₃ |
| —SCH₂CH₂OH | H | —OCH₃ |
| —SCH₃ | H | —OCH₃ |
| —SOCH₃ | H | —OCH₃ |

TABLE 1-continued

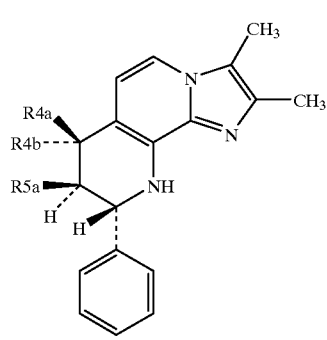

I**

| R4a | R4b | R5a |
|---|---|---|
| —SO$_2$CH$_3$ | H | —OCH$_3$ |
| —SCH$_2$CH$_3$ | H | —OCH$_3$ |
| —SOCH$_2$CH$_3$ | H | —OCH$_3$ |
| —SO$_2$CH$_2$CH$_3$ | H | —OCH$_3$ |
| —SCH$_2$CH$_2$CH$_3$ | H | —OCH$_3$ |
| —SO$_2$CH$_2$CH$_2$CH$_3$ | H | —OCH$_3$ |
| —SO$_2$CH$_2$CH$_2$CH$_3$ | H | —OCH$_3$ |
| —SCH(CH$_3$)$_2$ | H | —OCH$_3$ |
| —SOCH(CH$_3$)$_2$ | H | —OCH$_3$ |
| —SO$_2$CH(CH$_3$)$_2$ | H | —OCH$_3$ |
| —SCH$_2$COOCH$_2$CH$_3$ | H | —OCH$_3$ |
| —SOCH$_2$COOCH$_2$CH$_3$ | H | —OCH$_3$ |
| —SO$_2$CH$_2$COOCH$_2$CH$_3$ | H | —OCH$_3$ |
| —OCH$_2$CH$_2$SCH$_3$ | H | —OCH$_2$CH$_2$OCH$_3$ |
| —OCH$_2$CH$_2$SOCH$_3$ | H | —OCH$_2$CH$_2$OCH$_3$ |
| —OCH$_2$CH$_2$SO$_2$CH$_3$ | H | —OCH$_2$CH$_2$OCH$_3$ |
| —SCH$_2$CH$_2$OCH$_3$ | H | —OCH$_2$CH$_2$OCH$_3$ |
| —SOCH$_2$CH$_2$OCH$_3$ | H | —OCH$_2$CH$_2$OCH$_3$ |
| —SO$_2$CH$_2$CH$_2$OCH$_3$ | H | —OCH$_2$CH$_2$OCH$_3$ |
| —SOCH$_2$CH$_2$CH | H | —OCH$_2$CH$_2$OCH$_3$ |
| —SCH$_3$ | H | —OCH$_2$CH$_2$OCH$_3$ |
| —SOCH$_3$ | H | —OCH$_2$CH$_2$OCH$_3$ |
| —SO$_2$CH$_3$ | H | —OCH$_2$CH$_2$OCH$_3$ |
| —SCH$_2$CH$_3$ | H | —OCH$_2$CH$_2$OCH$_3$ |
| —SOCH$_2$CH$_3$ | H | —OCH$_2$CH$_2$OCH$_3$ |
| —SO$_2$CH$_2$CH$_3$ | H | —OCH$_2$CH$_2$OCH$_3$ |
| —SCH$_2$CH$_2$CH$_3$ | H | —OCH$_2$CH$_2$OCH$_3$ |
| —SOCH$_2$CH$_2$CH$_3$ | H | —OCH$_2$CH$_2$OCH$_3$ |
| —SO$_2$CH$_2$CH$_2$CH$_3$ | H | —OCH$_2$CH$_2$OCH$_3$ |
| —SCH(CH$_3$)$_2$ | H | —OCH$_2$CH$_2$OCH$_3$ |
| —SO$_2$CH(CH$_3$)$_2$ | H | —OCH$_2$CH$_2$OCH$_3$ |
| —SO$_2$CH(CH$_3$)$_2$ | H | —OCH$_2$CH$_2$OCH$_3$ |
| —SCH$_2$COOCH$_2$CH$_3$ | H | —OCH$_2$CH$_2$OCH$_3$ |
| —SOCH$_2$COOCH$_2$CH$_3$ | H | —OCH$_2$CH$_2$OCH$_3$ |
| —SO$_2$CH$_2$COOCH$_2$CH$_3$ | H | —OCH$_2$CH$_2$OCH$_3$ |
| —OCH$_2$CH$_2$SCH$_3$ | H | —OCH$_2$CH$_2$SCH$_3$ |
| —OCH$_2$CH$_2$SOCH$_3$ | H | —OCH$_2$CH$_2$SCH$_3$ |
| —OCH$_2$CH$_2$SO$_2$CH$_3$ | H | —OCH$_2$CH$_2$SCH$_3$ |
| —SCH$_2$CH$_2$OCH$_3$ | H | —OCH$_2$CH$_2$SCH$_3$ |
| —SOCH$_2$CH$_2$OCH$_3$ | H | —OCH$_2$CH$_2$SCH$_3$ |
| —SO$_2$CH$_2$CH$_2$OCH$_3$ | H | —OCH$_2$CH$_2$SCH$_3$ |
| —SCH$_2$CH$_2$CH | H | —OCH$_2$CH$_2$SCH$_3$ |
| —SCH$_3$ | H | —OCH$_2$CH$_2$SCH$_3$ |
| —SOCH$_3$ | H | —OCH$_2$CH$_2$SCH$_3$ |
| —SO$_2$CH$_3$ | H | —OCH$_2$CH$_2$SCH$_3$ |
| —SCH$_2$CH$_3$ | H | —OCH$_2$CH$_2$SCH$_3$ |
| —SOCH$_2$CH$_3$ | H | —OCH$_2$CH$_2$SCH$_3$ |
| —SO$_2$CH$_2$CH$_3$ | H | —OCH$_2$CH$_2$SCH$_3$ |
| —SCH$_2$CH$_2$CH$_3$ | H | —OCH$_2$CH$_2$SCH$_3$ |
| —SOCH$_2$CH$_2$CH$_3$ | H | —OCH$_2$CH$_2$SCH$_3$ |
| —SO$_2$CH$_2$CH$_2$CH$_3$ | H | —OCH$_2$CH$_2$SCH$_3$ |
| —SCH(CH$_3$)$_2$ | H | —OCH$_2$CH$_2$SCH$_3$ |
| —SO$_2$CH(CH$_3$)$_2$ | H | —OCH$_2$CH$_2$SCH$_3$ |
| —SO$_2$CH(CH$_3$)$_2$ | H | —OCH$_2$CH$_2$SCH$_3$ |
| —SCH$_2$COOCH$_2$CH$_3$ | H | —OCH$_2$CH$_2$SCH$_3$ |
| —SOCH$_2$COOCH$_2$CH$_3$ | H | —OCH$_2$CH$_2$SCH$_3$ |
| —SO$_2$CH$_2$COOCH$_2$CH$_3$ | H | —OCH$_2$CH$_2$SCH$_3$ |
| —OCH$_2$CH$_2$SCH$_3$ | H | —SCH$_2$CH$_2$OH |
| —OCH$_2$CH$_2$SOCH$_3$ | H | —SCH$_2$CH$_2$OH |

TABLE 1-continued

I**

| R4a | R4b | R5a |
|---|---|---|
| —OCH₂CH₂SO₂CH₃ | H | —SCH₂CH₂OH |
| —SCH₂CH₂OCH₃ | H | —SCH₂CH₂OH |
| —SOCH₂CH₂OCH₃ | H | —SCH₂CH₂OH |
| —SO₂CH₂CH₂OCH₃ | H | —SCH₂CH₂OH |
| —SCH₂CH₂OH | H | —SCH₂CH₂OH |
| —SCH₃ | H | —SCH₂CH₂OH |
| —SOCH₃ | H | —SCH₂CH₂OH |
| —SO₂CH₃ | H | —SCH₂CH₂OH |
| —SCH₂CH₃ | H | —SCH₂CH₂OH |
| —SOCH₂CH₃ | H | —SCH₂CH₂OH |
| —SO₂CH₂CH₃ | H | —SCH₂CH₂OH |
| —SCH₂CH₂CH₃ | H | —SCH₂CH₂OH |
| —SOCH₂CH₂CH₃ | H | —SCH₂CH₂OH |
| —SO₂CH₂CH₂CH₃ | H | —SCH₂CH₂OH |
| —SCH(CH₃)₂ | H | —SCH₂CH₂OH |
| —SOCH(CH₃)₂ | H | —SCH₂CH₂OH |
| —SO₂CH(CH₃)₂ | H | —SCH₂CH₂OH |
| —SCH₂COOCH₂CH₃ | H | —SCH₂CH₂OH |
| —SOCH₂COOCH₂CH₃ | H | —SCH₂CH₂OH |
| —SO₂CH₂COOCH₂CH₃ | H | —SCH₂CH₂OH |
| —OCH₂CH₂SCH₃ | H | —SCH₃ |
| —OCH₂CH₂SOCH₃ | H | —SCH₃ |
| —OCH₂CH₂SO₂CH₃ | H | —SCH₃ |
| —SCH₂CH₂OCH₃ | H | —SCH₃ |
| —SOCH₂CH₂OCH₃ | H | —SCH₃ |
| —SO₂CH₂CH₂OCH₃ | H | —SCH₃ |
| —SCH₂CH₂OH | H | —SCH₃ |
| —SCH₃ | H | —SCH₃ |
| —SOCH₃ | H | —SCH₃ |
| —SO₂CH₃ | H | —SCH₃ |
| —SCH₂CH₃ | H | —SCH₃ |
| —SOCH₂CH₃ | H | —SCH₃ |
| —SO₂CH₂CH₃ | H | —SCH₃ |
| —SCH₂CH₂CH₃ | H | —SCH₃ |
| —SOCH₂CH₂CH₃ | H | —SCH₃ |
| —SO₂CH₂CH₂CH₃ | H | —SCH₃ |
| —SCH(CH₃)₂ | H | —SCH₃ |
| —SOCH(CH₃)₂ | H | —SCH₃ |
| —SO₂CH(CH₃)₂ | H | —SCH₃ |
| —SCH₂COOCH₂CH₃ | H | —SCH₃ |
| —SOCH₂COOCH₂CH₃ | H | —SCH₃ |
| —SO₂CH₂COOCH₂CH₃ | H | —SCH₃ |
| —OCH₂CH₂SCH₃ | H | —SCH₂CH₂OCH₃ |
| —OCH₂CH₂SOCH₃ | H | —SCH₂CH₂OCH₃ |
| —OCH₂CH₂SO₂CH₃ | H | —SCH₂CH₂OCH₃ |
| —SCH₂CH₂OCH₃ | H | —SCH₂CH₂OCH₃ |
| —SOCH₂CH₂OCH₃ | H | —SCH₂CH₂OCH₃ |
| —SO₂CH₂CH₂OCH₃ | H | —SCH₂CH₂OCH₃ |
| —SCH₂CH₂OH | H | —SCH₂CH₂OCH₃ |
| —SCH₃ | H | —SCH₂CH₂OCH₃ |
| —SOCH₃ | H | —SCH₂CH₂OCH₃ |
| —SO₂CH₃ | H | —SCH₂CH₂OCH₃ |
| —SCH₂CH₃ | H | —SCH₂CH₂OCH₃ |
| —SOCH₂CH₃ | H | —SCH₂CH₂OCH₃ |
| —SO₂CH₂CH₃ | H | —SCH₂CH₂OCH₃ |
| —SCH₂CH₂CH₃ | H | —SCH₂CH₂OCH₃ |
| —SOCH₂CH₂CH₃ | H | —SCH₂CH₂OCH₃ |
| —SO₂CH₂CH₂CH₃ | H | —SCH₂CH₂OCH₃ |
| —SCH(CH₃)₂ | H | —SCH₂CH₂OCH₃ |

TABLE 1-continued

I**

| R4a | R4b | R5a |
|---|---|---|
| —SOCH(CH$_3$)$_2$ | H | —SCH$_2$CH$_2$OCH$_3$ |
| —SO$_2$CH(CH$_3$)$_2$ | H | —SCH$_2$CH$_2$OCH$_3$ |
| —SCH$_2$COOCH$_2$CH$_3$ | H | —SCH$_2$CH$_2$OCH$_3$ |
| —SOCH$_2$COOCH$_2$CH$_3$ | H | —SCH$_2$CH$_2$OCH$_3$ |
| —SO$_2$CH$_2$COOCH$_2$CH$_3$ | H | —SCH$_2$CH$_2$OCH$_3$ |
| H | —OCH$_2$CH$_2$SCH$_3$ | —OCH$_2$CH$_2$SCH$_3$ |
| H | —OCH$_3$CH$_2$SOCH$_3$ | —OCH$_2$CH$_2$SCH$_3$ |
| H | —OCH$_2$CH$_2$SO$_2$CH$_3$ | —OCH$_2$CH$_2$SCH$_3$ |
| H | —SCH$_2$CH$_2$OCH$_3$ | —OCH$_2$CH$_2$SCH$_3$ |
| H | —SOCH$_2$CH$_2$OCH$_3$ | —OCH$_2$CH$_2$SCH$_3$ |
| H | —SO$_2$CH$_2$CH$_2$OCH$_3$ | —OCH$_2$CH$_2$SCH$_3$ |
| H | —SCH$_2$CH$_2$OH | —OCH$_2$CH$_2$SCH$_3$ |
| H | —SCH$_3$ | —OCH$_3$CH$_2$SCH$_3$ |
| H | —SOCH$_3$ | —OCH$_2$CH$_2$SCH$_3$ |
| H | —SO$_2$CH$_3$ | —OCH$_2$CH$_2$SCH$_3$ |
| H | —SCH$_2$CH$_3$ | —OCH$_2$CH$_2$SCH$_3$ |
| H | —SOCH$_2$CH$_3$ | —OCH$_2$CH$_2$SCH$_3$ |
| H | —SO$_2$CH$_2$CH$_3$ | —OCH$_2$CH$_2$SCH$_3$ |
| H | —SCH$_2$CH$_2$CH$_3$ | —OCH$_2$CH$_2$SCH$_3$ |
| H | —SOCH$_2$CH$_2$CH$_3$ | —OCH$_2$CH$_2$SCH$_3$ |
| H | —SO$_3$CH$_2$CH$_2$CH$_3$ | —OCH$_2$CH$_2$SCH$_3$ |
| H | —SCH(CH$_3$)$_2$ | —OCH$_2$CH$_2$SCH$_3$ |
| H | —SOCH(CH$_3$)$_2$ | —OCH$_2$CH$_2$SCH$_3$ |
| H | —SO$_2$CH(CH$_3$)$_2$ | —OCH$_2$CH$_2$SCH$_3$ |
| H | —SCH$_2$COOCH$_2$CH$_3$ | —OCH$_2$CH$_2$SCH$_3$ |
| H | —SOCH$_2$COOCH$_2$CH$_3$ | —OCH$_2$CH$_2$SCH$_3$ |
| H | —SO$_2$CH$_2$COOCH$_2$CH$_3$ | —OCH$_2$CH$_2$SCH$_3$ |
| H | —OCH$_2$CH$_2$SCH$_3$ | —SCH$_2$CH$_2$OH |
| H | —OCH$_2$CH$_2$SOCH$_3$ | —SCH$_2$CH$_2$OH |
| H | —OCH$_2$CH$_2$SO$_2$CH$_3$ | —SCH$_2$CH$_2$OH |
| H | —SCH$_2$CH$_2$OCH$_3$ | —SCH$_2$CH$_2$OH |
| H | —SOCH$_2$CH$_2$OCH$_3$ | —SCH$_2$CH$_2$OH |
| H | —SO$_2$CH$_2$CH$_2$OCH$_3$ | —SCH$_2$CH$_2$OH |
| H | —SCH$_2$CH$_2$OH | —SCH$_2$CH$_2$OH |
| H | —SCH$_3$ | —SCH$_2$CH$_2$OH |
| H | —SOCH$_3$ | —SCH$_2$CH$_2$OH |
| H | —SO$_2$CH$_3$ | —SCH$_2$CH$_2$OH |
| H | —SCH$_2$CH$_3$ | —SCH$_2$CH$_2$OH |
| H | —SOCH$_2$CH$_3$ | —SCH$_2$CH$_2$OH |
| H | —SO$_2$CH$_2$CH$_3$ | —SCH$_2$CH$_2$OH |
| H | —SCH$_2$CH$_2$CH$_3$ | —SCH$_2$CH$_2$OH |
| H | —SOCH$_2$CH$_2$CH$_3$ | —SCH$_2$CH$_2$OH |
| H | —SO$_2$CH$_2$CH$_2$CH$_3$ | —SCH$_2$CH$_2$OH |
| H | —SCH(CH$_3$)$_2$ | —SCH$_2$CH$_2$OH |
| H | —SOCH(CH$_3$)$_2$ | —SCH$_2$CH$_2$OH |
| H | —SO$_2$CH(CH$_3$)$_2$ | —SCH$_2$CH$_2$OH |
| H | —SCH$_2$COOCH$_2$CH$_3$ | —SCH$_2$CH$_2$OH |
| H | —SOCH$_2$COOCH$_2$CH$_3$ | —SCH$_2$CH$_2$OH |
| H | —SO$_2$CH$_2$COOCH$_2$CH$_3$ | —SCH$_2$CH$_2$OH |
| H | —OCH$_2$CH$_2$SCH$_3$ | —SCH$_3$ |
| H | —OCH$_2$CH$_2$SOCH$_3$ | —SCH$_3$ |
| H | —OCH$_2$CH$_2$SO$_2$CH$_3$ | —SCH$_3$ |
| H | —SCH$_2$CH$_2$OCH$_3$ | —SCH$_3$ |
| H | —SOCH$_2$CH$_2$OCH$_3$ | —SCH$_3$ |
| H | —SO$_2$CH$_2$CH$_2$OCH$_3$ | —SCH$_3$ |
| H | —SCH$_2$CH$_2$OH | —SCH$_3$ |
| H | —SCH$_3$ | —SCH$_3$ |
| H | —SOCH$_3$ | —SCH$_3$ |
| H | —SO$_2$CH$_3$ | —SCH$_3$ |

TABLE 1-continued

I**

| R4a | R4b | R5a |
|---|---|---|
| H | —SCH$_2$CH$_3$ | —SCH$_3$ |
| H | —SOCH$_2$CH$_3$ | —SCH$_3$ |
| H | —SO$_2$CH$_2$CH$_3$ | —SCH$_3$ |
| H | —SCH$_2$CH$_2$CH$_3$ | —SCH$_3$ |
| H | —SOCH$_2$CH$_2$CH$_3$ | —SCH$_3$ |
| H | —SO$_2$CH$_2$CH$_2$CH$_3$ | —SCH$_3$ |
| H | —SCH(CH$_3$)$_2$ | —SCH$_3$ |
| H | —SOCH(CH$_3$)$_2$ | —SCH$_3$ |
| H | —SO$_2$CH(CH$_3$)$_2$ | —SCH$_3$ |
| H | —SCH$_2$COOCH$_2$CH$_3$ | —SCH$_3$ |
| H | —SOCH$_2$COOCH$_2$CH$_3$ | —SCH$_3$ |
| H | —SO$_2$CH$_2$COOCH$_2$CH$_3$ | —SCH$_3$ |
| H | —OCH$_2$CH$_2$SCH$_3$ | —SCH$_2$CH$_2$OCH$_3$ |
| H | —OCH$_2$CH$_2$SOCH$_3$ | —SCH$_2$CH$_2$OCH$_3$ |
| H | —OCH$_2$CH$_2$SO$_2$CH$_3$ | —SCH$_2$CH$_2$OCH$_3$ |
| H | —SCH$_2$CH$_2$OCH$_3$ | —SCH$_2$CH$_2$OCH$_3$ |
| H | —SOCH$_2$CH$_2$OCH$_3$ | —SCH$_2$CH$_2$OCH$_3$ |
| H | —SO$_2$CH$_2$CH$_2$OCH$_3$ | —SCH$_2$CH$_2$OCH$_3$ |
| H | —SCH$_2$CH$_2$OH | —SCH$_2$CH$_2$OCH$_3$ |
| H | —SCH$_3$ | —SCH$_2$CH$_2$OCH$_3$ |
| H | —SOCH$_3$ | —SCH$_2$CH$_2$OCH$_3$ |
| H | —SO$_2$CH$_3$ | —SCH$_2$CH$_2$OCH$_3$ |
| H | —SCH$_2$CH$_3$ | —SCH$_2$CH$_2$OCH$_3$ |
| H | —SOCH$_2$CH$_3$ | —SCH$_2$CH$_2$OCH$_3$ |
| H | —SO$_2$CH$_2$CH$_3$ | —SCH$_2$CH$_2$OCH$_3$ |
| H | —SCH$_2$CH$_2$CH$_3$ | —SCH$_2$CH$_2$OCH$_3$ |
| H | —SOCH$_2$CH$_2$CH$_3$ | —SCH$_2$CH$_2$OCH$_3$ |
| H | —SO$_2$CH$_2$CH$_2$CH$_3$ | —SCH$_2$CH$_2$OCH$_3$ |
| H | —SCH(CH$_3$)$_2$ | —SCH$_2$CH$_2$OCH$_3$ |
| H | —SOCH(CH$_3$)$_2$ | —SCH$_2$CH$_2$OCH$_3$ |
| H | —SO$_2$CH(CH$_3$)$_2$ | —SCH$_2$CH$_2$OCH$_3$ |
| H | —SCH$_2$COOCH$_2$CH$_3$ | —SCH$_2$CH$_2$OCH$_3$ |
| H | —SOCH$_2$COOCH$_2$CH$_3$ | —SCH$_2$CH$_2$OCH$_3$ |
| H | —SO$_2$CH$_2$COOCH$_2$CH$_3$ | —SCH$_2$CH$_2$OCH$_3$ |
| H | —OCH$_3$ | —OCH$_2$CH$_2$SCH$_3$ |
| H | —OCH$_3$ | —OCH$_2$CH$_2$SOCH$_3$ |
| H | —OCH$_3$ | —OCH$_2$CH$_2$SO$_2$CH$_3$ |
| H | —OCH$_3$ | —SCH$_2$CH$_2$OCH$_3$ |
| H | —OCH$_3$ | —SOCH$_2$CH$_2$OCH$_3$ |
| H | —OCH$_3$ | —SO$_2$CH$_2$CH$_2$OCH$_3$ |
| H | —OCH$_3$ | —SCH$_2$CH$_2$OH |
| H | —OCH$_3$ | —SCH$_3$ |
| H | —OCH$_3$ | —SOCH$_3$ |
| H | —OCH$_3$ | —SO$_2$CH$_3$ |
| H | —OCH$_3$ | —SCH$_2$CH$_3$ |
| H | —OCH$_3$ | —SOCH$_2$CH$_3$ |
| H | —OCH$_3$ | —SO$_2$CH$_2$CH$_3$ |
| H | —OCH$_3$ | —SCH$_2$CH$_2$CH$_3$ |
| H | —OCH$_3$ | —SOCH$_2$CH$_2$CH$_3$ |
| H | —OCH$_3$ | —SO$_2$CH$_2$CH$_2$CH$_2$ |
| H | —OCH$_3$ | —SCH(CH$_3$)$_2$ |
| H | —OCH$_3$ | —SOCH(CH$_3$)$_2$ |
| H | —OCH$_3$ | —SO$_2$CH(CH$_3$)$_2$ |
| H | —OCH$_3$ | —SCH$_2$COOCH$_2$CH$_3$ |
| H | —OCH$_3$ | —SOCH$_2$COOCH$_2$CH$_3$ |
| H | —OCH$_3$ | —SO$_2$CH$_2$COOCH$_2$CH$_3$ |
| H | —OCH$_2$CH$_2$OCH$_3$ | —OCH$_2$CH$_2$SCH$_3$ |
| H | —OCH$_2$CH$_2$OCH$_3$ | —OCH$_2$CH$_2$SOCH$_3$ |
| H | —OCH$_2$CH$_2$OCH$_3$ | —OCH$_2$CH$_2$SO$_2$CH$_3$ |

TABLE 1-continued

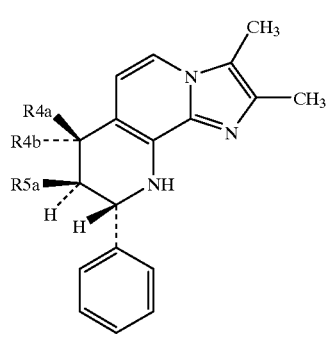

I**

| R4a | R4b | R5a |
|---|---|---|
| H | —OCH$_2$CH$_2$OCH$_3$ | —SCH$_2$CH$_2$OCH$_3$ |
| H | —OCH$_2$CH$_2$OCH$_3$ | —SOCH$_2$CH$_2$OCH$_3$ |
| H | —OCH$_2$CH$_2$OCH$_3$ | —SO$_2$CH$_2$CH$_2$OCH$_3$ |
| H | —OCH$_2$CH$_2$OCH$_3$ | —SCH$_2$CH$_2$OH |
| H | —OCH$_2$CH$_2$OCH$_3$ | —SCH$_3$ |
| H | —OCH$_2$CH$_2$OCH$_3$ | —SOCH$_3$ |
| H | —OCH$_2$CH$_2$OCH$_3$ | —SO$_2$CH$_3$ |
| H | —OCH$_2$CH$_2$OCH$_3$ | —SCH$_2$CH$_3$ |
| H | —OCH$_2$CH$_2$OCH$_3$ | —SOCH$_2$CH$_3$ |
| H | —OCH$_2$CH$_2$OCH$_3$ | —SO$_2$CH$_2$CH$_3$ |
| H | —OCH$_2$CH$_2$OCH$_3$ | —SCH$_2$CH$_2$CH$_3$ |
| H | —OCH$_2$CH$_2$OCH$_3$ | —SOCH$_2$CH$_2$CH$_3$ |
| H | —OCH$_2$CH$_2$OCH$_3$ | —SO$_2$CH$_2$CH$_2$CH$_3$ |
| H | —OCH$_2$CH$_2$OCH$_3$ | —SCH(CH$_3$)$_2$ |
| H | —OCH$_2$CH$_2$OCH$_3$ | —SOCH(CH$_3$)$_2$ |
| H | —OCH$_2$CH$_2$OCH$_3$ | —SO$_2$CH(CH$_3$)$_2$ |
| H | —OCH$_2$CH$_2$OCH$_3$ | —SCH$_2$COOCH$_2$CH$_3$ |
| H | —OCH$_2$CH$_2$OCH$_3$ | —SOCH$_2$COOCH$_2$CH$_3$ |
| H | —OCH$_2$CH$_2$OCH$_3$ | —SO$_2$CH$_2$COOCH$_2$CH$_3$ |
| —OCH$_3$ | H | —OCH$_2$CH$_2$SCH$_3$ |
| —OCH$_3$ | H | —OCH$_2$CH$_2$SOCH$_3$ |
| —OCH$_3$ | H | —OCH$_2$CH$_2$SO$_2$CH$_3$ |
| —OCH$_3$ | H | —SCH$_2$CH$_2$OCH$_3$ |
| —OCH$_3$ | H | —SOCH$_2$CH$_2$OCH$_3$ |
| —OCH$_3$ | H | —SO$_2$CH$_2$CH$_2$OCH$_3$ |
| —OCH$_3$ | H | —SCH$_2$CH$_2$OH |
| —OCH$_3$ | H | —SCH$_3$ |
| —OCH$_3$ | H | —SOCH$_3$ |
| —OCH$_3$ | H | —SO$_2$CH$_3$ |
| —OCH$_3$ | H | —SCH$_2$CH$_3$ |
| —OCH$_3$ | H | —SOCH$_2$CH$_3$ |
| —OCH$_3$ | H | —SO$_2$CH$_2$CH$_3$ |
| —OCH$_3$ | H | —SCH$_2$CH$_2$CH$_3$ |
| —OCH$_3$ | H | —SOCH$_2$CH$_2$CH$_3$ |
| —OCH$_3$ | H | —SO$_2$CH$_2$CH$_2$CH$_3$ |
| —OCH$_3$ | H | —SCH(CH$_3$)$_2$ |
| —OCH$_3$ | H | —SOCH(CH$_3$)$_2$ |
| —OCH$_3$ | H | —SO$_2$CH(CH$_3$)$_2$ |
| —OCH$_3$ | H | —SCH$_2$COOCH$_2$CH$_3$ |
| —OCH$_3$ | H | —SOCH$_2$COOCH$_2$CH$_3$ |
| —OCH$_3$ | H | —SO$_2$CH$_2$COOCH$_2$CH$_3$ |
| —OCH$_2$CH$_2$OCH$_3$ | H | —OCH$_2$CH$_2$SCH$_3$ |
| —OCH$_2$CH$_2$OCH$_3$ | H | —OCH$_2$CH$_2$SOCH$_3$ |
| —OCH$_2$CH$_2$OCH$_3$ | H | —OCH$_2$CH$_2$SO$_2$CH$_2$ |
| —OCH$_2$CH$_2$OCH$_3$ | H | —SCH$_2$CH$_2$OCH$_3$ |
| —OCH$_2$CH$_2$OCH$_3$ | H | —SOCH$_2$CH$_2$OCH$_3$ |
| —OCH$_2$CH$_2$OCH$_3$ | H | —SO$_2$CH$_2$CH$_2$OCH$_3$ |
| —OCH$_2$CH$_2$OCH$_3$ | H | —SCH$_2$CH$_2$OH |
| —OCH$_2$CH$_2$OCH$_3$ | H | —SCH$_3$ |
| —OCH$_2$CH$_2$OCH$_3$ | H | —SOCH$_3$ |
| —OCH$_2$CH$_2$OCH$_3$ | H | —SO$_2$CH$_3$ |
| —OCH$_2$CH$_2$OCH$_3$ | H | —SCH$_2$CH$_3$ |
| —OCH$_2$CH$_2$OCH$_3$ | H | —SOCH$_2$CH$_3$ |
| —OCH$_2$CH$_2$OCH$_3$ | H | —SO$_2$CH$_2$CH$_3$ |
| —OCH$_2$CH$_2$OCH$_3$ | H | —SCH$_2$CH$_2$CH$_3$ |
| —OCH$_2$CH$_2$OCH$_3$ | H | —SOCH$_2$CH$_2$CH$_3$ |
| —OCH$_2$CH$_2$OCH$_3$ | H | —SO$_2$CH$_2$CH$_2$CH$_3$ |
| —OCH$_2$CH$_2$OCH$_3$ | H | —SCH(CH$_3$)$_2$ |
| —OCH$_2$CH$_2$OCH$_3$ | H | —SOCH(CH$_3$)$_2$ |

TABLE 1-continued

I**

[Structure: tetrahydroimidazo[1,2-h][1,7]naphthyridine core with CH3 groups, R4a, R4b, R5a substituents and phenyl]

| R4a | R4b | R5a |
|---|---|---|
| —OCH$_2$CH$_2$OCH$_3$ | H | —SO$_2$CH(CH$_3$)$_2$ |
| —OCH$_2$CH$_2$OCH$_3$ | H | —SCH$_2$COOCH$_2$CH$_3$ |
| —OCH$_2$CH$_2$OCH$_3$ | H | —SOCH$_2$COOCH$_2$CH$_3$ |
| —OCH$_2$CH$_2$OCH$_3$ | H | —SO$_2$CH$_2$COOCH$_2$CH$_3$ |

The compounds according to the invention are prepared, for example, starting from the compounds of the formula I known from WO98/42707 in which at least one of the substituents R4a, R4b, R5a and R5b is hydroxyl (referred to as "starting materials" hereinbelow). Starting with the starting materials, the compounds according to the invention can be prepared by various routes, depending on which end product is desired, for example as outlined below:

a) by acid-catalyzed etherification of the starting materials with compounds of the formula R4'-H or R5'-H.

b) by reacting the starting materials (if appropriate after they have been sulfidized) with compounds of the formula R9-S(O)$_n$—(CH$_2$)$_m$-Hal, HO—(CH$_2$)$_m$-Hal, R9-O—(CH$_2$)$_m$-Hal, R9-S(O)$_p$—(CH$_2$)$_m$-Hal, R9-Hal, R9-S(O)$_n$-alk1-Hal, HO-alk1-Hal, R9-O-alk1-Hal or R9S(O)$_p$-alk1-Hal or R10-S(O)$_r$—(CH$_2$)$_q$-Hal, HO—(CH$_2$)$_q$-Hal, R10-O—(CH$_2$)$_q$-Hal, R10-S(O)$_r$—(CH$_2$)$_q$-Hal, R10-Hal, R10-S(O)$_r$-alk2-Hal, HO-alk2-Hal, R10-O-alk2-Hal or R10-S(O)$_r$-alk2-Hal, where Hal is a halogen atom, preferably a chlorine, bromine or iodine atom, preferably in the presence of an auxiliary base or after prior deprotonation of the starting material.

Depending on the nature of the radical R4' or R5', it may be advantageous not to introduce the entire radical R4' or R5' into the starting materials by the appropriate reaction. Rather, it is also feasible to employ a two- or multi-step procedure, as described in an exemplary manner in the European Patent Application 235 575, for example.

For the compounds of the formula I according to the invention in which n, p, r and/or t are different from the number 0, the reaction according to a) or b) is, if appropriate, followed by oxidation.

The oxidation of the sulfides to the sulfoxides or sulfones is carried out under the conditions known to the person skilled in the art for oxidizing sulfides to sulfoxides and sulfones respectively, [see, for example, J. Drabowicz and M. Mikolajczyk, Organic preparations and procedures int. 14(1–2), 45–89 (1982) or E. Block in S. Patai, The Chemistry of Functional Groups, Supplement E. Part 1, pp. 539–608, John Wiley and Sons (Interscience Publication), 1980]. Suitable oxidizing agents are all reagents which are customarily used for oxidizing sulfides to sulfoxides or sulfones.

Sulfoxides are optically active compounds, so that for n, p, r and/or t=1, one or more further chiral centers are introduced into the molecule. With respect to the sulfoxides, the invention therefore also embraces both the enantiomers and diastereomers and their mixtures and racemates. The enantiomers can be separated in a manner known per se (for example by preparing and separating corresponding diastereoisomeric compounds).

The compounds of the formulae R4'-H, R5'-H, R9-S(O)$_n$—(CH2)$_m$-Hal, HO—(CH2)$_m$-Hal, R9-O—(CH$_2$)$_m$-Hal, R9-S(O)$_p$—(CH$_2$)$_m$-Hal, R9-Hal, R9-S(O)$_n$-alk1-Hal, HO-alk1-Hal, R9-O-alk1-Hal, R9-S(O)$_p$-alk1-Hal, R10-S(O)$_r$—(CH$_2$)$_q$-Hal, HO—(CH$_2$)$_q$-Hal, R10-O—(CH$_2$)$_q$-Hal, R10-S(O)$_r$—(CH$_2$)$_q$-Hal, R10-Hal, R10-S(O)$_r$-alk2-Hal, HO-alk2-Hal, R10-O-alk2-Hal, R10-S(O)$_r$-alk2-Hal and the compounds required for their preparation are known, or they can be prepared in a manner known per se.

The following examples illustrate the invention in more detail, without limiting it. The compounds according to the invention can be prepared in a manner analogous to that described in the examples. The abbreviation RT stands for room temperature, h stands for hour(s), m.p. stands for melting point and decomp. stands for decomposition.

EXAMPLES 1. (7R,8R,9R)-2,3-dimethyl-8-hydroxy-7-(2-methylthioethyloxy)-9-phenyl-7,8,9,10-tetrahydroimidazo[1,2-h][1,7]naphthyridine 1 g of (7R,8R,9R)-7,8-dihydroxy-2,3-dimethyl-9-phenyl-7,8,9,10-tetrahydroimidazo[1,2-h][1,7]naphthyridine, dissolved in 30 ml of dioxane and 5 ml of dimethyl-formamide, is admixed with 0.63 g of concentrated sulfuric acid and 1 g of 2-methylmercaptoethanol. The mixture is stirred at RT for 3 h, poured into ice-water (200 ml), adjusted to pH 8 using 2 N aqueous sodium hydroxide solution and extracted three times with methylene chloride. The solvent is stripped off under reduced pressure and the oily residue that remains is purified on silica gel (mobile phase: diethyl ether). This gives 80 mg of the title compound of m.p. 118–9° C. (diisopropyl ether).

2. (7S,8R,9R)-2,3-dimethyl-8-hydroxy-7-(2-methylthioethyloxy)9-phenyl-7,8,9,10-tetrahydroimidazo[1,2-h][1,7]naphthyridine The mother liquor from Example 1 gives, after purification on silica gel (mobile phase: diethyl ether), 40 mg of the title compound of m.p. 109–10° C.

3. (7R,8R,9R)-2,3-dimethyl-8-hydroxy-7-(2-methylsulphinylethoxy)-9phenyl-7,8,9,10-tetrahydroimidazo[1,2-h][1,7]naphthyridine 130 mg of sodium metaperiodate, dissolved in 1 ml of water, is added to a solution of 200 mg of (7R,8R,9R)-2,3-dimethyl-8-hydroxy-7-(2-methylthioethoxy)-9-phenyl-7,8,9,10-tetrahydroimidazo[1,2-h]-[1,7]naphthyridine in 5 ml of methanol. After two hours stirring at room temperature, 50 ml of water are added. The mixture is extracted three times with dichloromethane, the organic phases are collectively washed with water and dried over sodium sulphate. The solvent is removed in vacuo and the remaining residue is purified by chromatography on silica gel (eluent: ethylacetate/methanol=10/1). 100 mg of the title compound of m.p. 105–106° C. are obtained.

4. (7S,8R,9R)-2,3-dimethyl-8-hydroxy-7-(2-methylsulphinylethoxy)-9-phenyl-7,8,9,10-tetrahydroimidazo[1,2-h][1,7]naphthyridine 80 mg of the title compound of m.p. 85–87° C. are obtained by oxidation of 200 mg of (7S,8R,9R)-2,3-dimethyl-8-hydroxy-7-(2-methylthioethoxy)-9-phenyl-7,8,9,10-tetrahydro-imidazo[1,2-h][1,7]naphthyridine analogously to Example 3.

5. (7R,8R,9R)-2,3dimethyl-8-hydroxy-7-(ethylthio)-9-phenyl-7,8,9,10-tetrahydro-imidazo[1,2-h][1,7]naphthyridine 1.9 g of concentrated sulphuric acid are added slowly at room temperature with stirring to 3 g of (7R,8R,9R)-7,8-dihydroxy-2,3-dimethyl-9-phenyl-7,8,9,10-tetrahydroimidazo[1,2-h][1,7]naphthyridine, dissolved in a mixture of 40 ml of dry dioxan and 4 ml of ethylsulfide: The temperature is brought to 50° C. by external heating and is then kept for 15 min. After cooling to room temperature, the mixture is poured into 300 g of a mixture of crushed ice and water. The pH is adjusted to neutral by adding aqueous 2N sodium hydroxide solution. The mixture is extracted three times (50 ml each) with ethyl acetate, the organic layers are collectively washed with water and dried over potassium carbonate. The solvent is stripped off under reduced pressure and the solid residue that remains is purified by chromatography on silica gel (mobile phase: diethyl ether). 700 mg of the title compound of m.p. 220–223° C. are obtained after crystallisation from 2-propanol.

6. (7S,8R,9R)-2,3-dimethyl-8-hydroxy-7-(ethylthio)-9-phenyl-7,8,9,10-tetrahydro-imidazo[1,2-h][1,7]naphthyridine 400 mg of the title-compound of m.p. 235–236° C. are obtained after crystallisation from isopropyl acetate by chromatographic purification on silica gel of the solid residue of Example 5.

COMMERCIAL UTILITY

The compounds of the formula I and their salts have valuable pharmacological properties which make them commercially utilizable. In particular, they exhibit marked inhibition of gastric acid secretion and an excellent gastric and intestinal protective action in warm-blooded animals, in particular humans. In this connection, the compounds according to the invention are distinguished by a high selectivity of action, an advantageous duration of action, a particularly good enteral activity, the absence of significant side effects and a large therapeutic range.

"Gastric and intestinal protection" in this connection is understood as meaning the prevention and treatment of gastrointestinal diseases, in particular of gastrointestinal inflammatory diseases and lesions (such as, for example, gastric ulcer, duodenal ulcer, gastritis, hyperacidic or medicament-related functional dyspepsia), which can be caused, for example, by microorganisms (e.g. Helicobacter pylori), bacterial toxins, medicaments (e.g. certain antiinflammatories and antirheumatics), chemicals (e.g. ethanol), gastric acid or stress situations.

In their excellent properties, the compounds according to the invention surprisingly prove to be clearly superior to the compounds known from the prior art in various models in which the antiulcerogenic and the antisecretory properties are determined. On account of these properties, the compounds of the formula I and their pharmacologically acceptable salts are outstandingly suitable for use in human and veterinary medicine, where they are used, in particular, for the treatment and/or prophylaxis of disorders of the stomach and/or intestine. A further subject of the invention are therefore the compounds according to the invention for use in the treatment and/or prophylaxis of the abovementioned diseases.

The invention likewise includes the use of the compounds according to the invention for the production of medicaments which are employed for the treatment and/or prophylaxis of the abovementioned diseases.

The invention furthermore includes the use of the compounds according to the invention for the treatment and/or prophylaxis of the abovementioned diseases.

A further subject of the invention are medicaments which comprise one or more compounds of the formula I and/or their pharmacologically acceptable salts.

The medicaments are prepared by processes which are known per se and familiar to the person skilled in the art. As medicaments, the pharmacologically active compounds according to the invention (=active compounds) are either employed as such, or preferably in combination with suitable pharmaceutical auxiliaries or excipients in the form of tablets, coated tablets, capsules, suppositories, patches (e.g. as TTS), emulsions, suspensions or solutions, the active compound content advantageously being between 0.1 and 95% and it being possible to obtain a pharmaceutical administration form exactly adapted to the active compound and/or to the desired onset of action (e.g. a sustained-release form or an enteric form) by means of the appropriate selection of the auxiliaries and excipients.

The auxiliaries and excipients which are suitable for the desired pharmaceutical formulations are known to the person skilled in the art on the basis of his/her expert knowledge. In addition to solvents, gel-forming agents, suppository bases, tablet auxiliaries and other active compound excipients, it is possible to use, for example, antioxidants, dispersants, emulsifiers, antifoams, flavor corrigents, preservatives, solubilizers, colorants or, in particular, permeation promoters and complexing agents (e.g. cyclodextrins).

The active compounds can be administered orally, parenterally or percutaneously.

In general, it has proven advantageous in human medicine to administer the active compound(s) in the case of oral administration in a daily dose of approximately 0.01 to approximately 20, preferably 0.05 to 5, in particular 0.1 to 1.5, mg/kg of body weight, if appropriate in the form of several, preferably 1 to 4, individual doses to achieve the desired result. In the case of a parenteral treatment, similar or (in particular in the case of the intravenous administration of the active compounds), as a rule, lower doses can be used. The establishment of the optimal dose and manner of administration of the active compounds necessary in each case can easily be carried out by any person skilled in the art on the basis of his/her expert knowledge.

If the compounds and/or their salts according to the invention are to be used for the treatment of the abovementioned diseases, the pharmaceutical preparations can also contain one or more pharmacologically active constituents of other groups of medicaments, for example: tranquilizers, (for example from the group of the benzodiazepines, for example diazepam), spasmolytics (for example, bietamiverine or camylofin), anticholinergics, (for example, oxyphencyclimine or phencarbamide), local anesthetics, (for example, tetracaine or procaine), and, if appropriate, also enzymes, vitamins or amino acids.

To be emphasized in this connection is in particular the combination of the compounds according to the invention with pharmaceuticals which inhibit acid secretion, such as, for example, $H_2$ blockers (e.g. cimetidine, ranitidine), $H^+/K^+$ ATPase inhibitors (e.g. omeprazole, pantoprazole), or further with so-called peripheral anticholinergics (e.g. pirenzepine, telenzepine) and with gastrin antagonists with the aim of increasing the principal action in an additive or super-additive sense and/or of eliminating or of decreasing the side effects, or further the combination with antibacterially active substances (such as, for example, cephalosporins, tetracyclines, penicillins, macrolides, nitroimidazoles or alternatively bismuth salts) for the control of Helicobacter pylon. Suitable antibacterial co-components which may be mentioned are, for example, meziocillin, ampicillin, amoxicillin, cefalothin, cefoxitin, cefotaxim, imipenem, gentamycin, amikacin, erythromycin, ciprofloxacin, metronidazole, clarithromycin, azithromycin and combinations thereof (for example clarithromycin+metronidazole).

PHARMACOLOGY

The excellent gastric protective action and the gastric acid secretion-inhibiting action of the compounds according to the invention can be demonstrated in investigations on animal experimental models. The compounds according to the invention investigated in the model mentioned below have been provided with numbers which correspond to the numbers of these compounds in the examples.

Testing of the Secretion-inhibiting Action on the Perfused Rat Stomach

In Table A which follows, the influence of the compounds according to the invention on the pentagastrin-stimulated acid secretion of the perfused rat stomach after intravenous administration in vivo is shown.

TABLE A

| No. | Dose ($\mu$mol/kg) i.v. | Inhibition of acid secretion (%) |
|---|---|---|
| 1 | 3 | 100 |
| 5 | 3 | 100 |

Methodology

The abdomen of anesthetized rats (CD rat, female, 200–250 g; 1.5 g/kg i.m. urethane) was opened after tracheotomy by a median upper abdominal incision and a PVC catheter was fixed transorally in the esophagus and another via the pylorus such that the ends of the tube just projected into the gastric lumen. The catheter leading from the pylorus led outwards into the right abdominal wall through a side opening.

After thorough rinsing (about 50–100 ml), warm (37° C.) physiological NaCl solution was continuously passed through the stomach (0.5 ml/min, pH 6.8–6.9; Braun-Unita 1). The pH (pH meter 632, glass electrode EA 147; $\phi$=5 mm, Metrohm) and, by titration with a freshly prepared 0.01 N NaOH solution to pH 7 (Dosimat 665 Metrohm), the secreted HCl were determined in the effluent in each case collected at an interval of 15 minutes.

The gastric secretion was stimulated by continuous infusion of 1 $\mu$g/kg (=1.65 ml/h) of i.v. pentagastrin (left femoral vein) about 30 min after the end of the operation (i.e. after determination of 2 preliminary fractions). The substances to be tested were administered intravenously in a 1 ml/kg liquid volume 60 min after the start of the continuous pentagastrin infusion.

The body temperature of the animals was kept at a constant 37.8–38° C. by infrared irradiation and heat pads (automatic, stepless control by means of a rectal temperature sensor).

What is claimed is:
1. A compound of the formula I

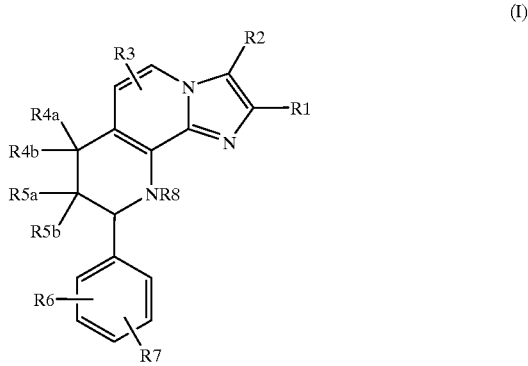

in which
R1 is 1–4C-alkyl,
R2 is 1–4C-alkyl or hydroxy-1–4C-alkyl,
R3 is hydrogen or halogen,
one of the substituents R4a and R4b is hydrogen and the other is hydrogen, hydroxyl, 1–4C-alkoxy, 1–4C-alkoxy-1–4C-alkoxy, 1–4C-alkylcarbonyloxy or the radical R4', or R4a and R4b together are O (oxygen), where,
R4' is
—O—$(CH_2)_m$S(O)$_n$—R9,
—S(O)$_n$—$(CH_2)_m$—OH,
—S(O)$_n$—$(CH_2)_m$—O—R9,
—S(O)$_n$—$(CH_2)_m$—S(O)$_p$—R9,
—O-alk1-S(O)$_n$—R9,
—S(O)$_n$—R9,
—S(O)$_n$-alk1-OH,
—S(O)$_n$-alk1-O-R9 or
—S(O)$_n$-alk1-S(O)$_p$-R9,
in which
R9 is 1–7C-alkyl, halo-1–4C-alkyl, hydroxy-1–4C-alkyl, 1–4C-alkoxy-1–4C-alkyl, carboxy-1–4C-alkyl, 1–4C-alkoxycarbonyl-1–4C-alkyl or di-1–4C-alkylamino-1–4C-alkyl, Ar or Ar-1–4C-alkyl, where Ar is phenyl or substituted phenyl having one, two or three identical or different substituents selected from the group consisting of 1–4C-alkyl, 1–4C-alkoxy, 1–4C-alkylcarbonyl, 1–4C-alkoxycarbonyl, halogen, trifluoromethyl, difluoromethoxy, trifluoromethoxy, amino, 1–4C-alkoxycarbonylamino, 1–4C-alkoxy-1–4C-alkoxycarbonylamino and nitro, alk1 is 1–4C-alkyl-, hydroxyl-, oxo-, carboxyl-, halogen-, amino-, 1–4C-alkoxycarbonylamino- or phenyl-substituted 2–7C-alkylene or 3–4C-alkenylene, m is an integer from 2 to 7, n is the number 0, 1 or 2 and p is the number 0, 1 or 2, one of the substituents R5a and R5b is hydrogen and the other is hydrogen, hydroxyl, 1–4C-alkoxy, 1–4C-alkoxy-1–4C-alkoxy, 1–4C-alkylcarbonyloxy or the radical R5', or R5a and R5b together are O (oxygen)

where

R5' is

—O—(CH$_2$)$_q$—S(O)$_r$—R10,
—S(O)$_r$—(CH$_2$)$_q$—OH,
—S(O)$_r$—(CH$_2$)$_q$—O—R10,
—S(O)$_r$(CH$_2$)$_q$—S(O)$_t$—R10,
—O-alk2-S(O)$_r$—R10,
—S(O)$_r$—R10,
—S(O)$_r$-alk2-OH,
—S(O)$_r$alk2-O—R10 or
—S(O)$_r$-alk2-S(O)$_t$—R10, in which R10 is 1–7C-alkyl, halo-1–4C-alkyl, hydroxy-1–4C-alkyl, 1–4C-alkoxy-1–4C-alkyl, carboxy-1–4C-alkyl, 1–4C-alkoxycarbonyl-1–4C-alkyl or di-1–4C-alkylamino-1–4C-alkyl, Ar or Ar-1–4C-alkyl, where Ar is phenyl or substituted phenyl having one, two or three identical or different substituents selected from the group consisting of 1–4C-alkyl, 1–4C-alkoxy, 1–4C-alkylcarbonyl, 1–4C-alkoxycarbonyl, halogen, trifluoromethyl, difluoromethoxy, trifluoromethoxy, amino, 1–4C-alkoxycarbonylamino, 1–4C-alkoxy-1–4C-alkoxycarbonylamino and nitro, alk2 is 1–4C-alky-, hydroxyl-, oxo-, carboxyl-, halogen-, amino-, 1–4C-alkoxycarbonylamino- or phenyl-substituted 2–7C-alkylene or 3–4C-alkenylene, q is an integer from 2 to 7, r is the number 0, 1 or 2 and t is the number 0, 1 or 2, R6 is hydrogen, halogen, 1–4C-alkyl, 1–4C-alkoxy, 1–4C-alkoxycarbonylamino, 1–4C-alkoxy-1–4C-alkoxycarbonylamino or trifluoromethyl, R7 is hydrogen, halogen, 1–4C-alkyl or 1–4C-alkoxy and R8 is hydrogen or 1–4C-alkyl, and its salts, where one of the substituents R4a and R4b has to be R4' and/or one of the substituents R5a and R5b has to be R5'.

2. A compound as claimed in claim 1, of the formula I*

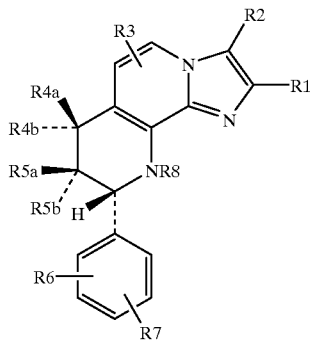

(I*)

in which

R1 is 1–4C-alkyl,

R2 is 1–4C-alkyl or hydroxy-1–4C-alkyl,

R3 is hydrogen, one of the substituents R4a and R4b is hydrogen and the other is hydrogen, hydroxyl, 1–4C-alkoxy, 1–4C-alkoxy-1–4C-alkoxy or the radical R4', where R4' is —O—(CH$_2$)$_m$—S(O)$_n$—R9,
—S(O)$_n$—(CH$_2$)$_m$—OH,
—S(O)$_n$—(CH$_2$)$_m$—O—R9,
—S(O)$_n$—(CH$_2$)$_m$—S(O)$_p$—R9 or
—S(O)$_n$—R9, in which R9 is 1–7C-alkyl, halo-1–4 C-alkyl, hydroxy-1–4C-alkyl or 1–4C-alkoxy-1–4C-alkyl, m is an integer from 2 to 7, n is the number 0, 1 or 2 and p is the number 0, 1 or 2, one of the substituents R5a and R5b is hydrogen and the other is hydrogen, hydroxyl, 1–4C-alkoxy, 1–4C-alkoxy-1–4C-alkoxy or the radical R5', where R5' is —O—(CH$_2$)$_q$—S(O)$_r$—R10,
—S(O)$_r$—(CH$_2$)$_q$—OH,
—S(O)$_r$(CH$_2$)$_q$—O—R10,
—S(O)$_r$—(CH$_2$)$_q$—S(O)$_t$—R10 or
—S(O)$_r$—R10, in which R10 is 1–7C-alkyl, halo-1–4C-alkyl, hydroxy-1–4C-alkyl or 1–4C-alkoxy-1–4C-alkyl, q is an integer from 2 to 7, r is the number 0, 1 or 2 and t is the number 0, 1 or 2, R6 is hydrogen, halogen or trifluoromethyl, R7 is hydrogen or halogen and R8 is hydrogen, and its salts, where one of the substituents R4a and R4b has to be R4' and/or one of the substituents R5a and R5b has to be R5'.

3. A compound I* as claimed in claim 2 in which

R1 is 1–4C-alkyl,

R2 is 1–4C-alkyl,

R3 is hydrogen,
one of the substituents R4a and R4b is hydrogen and the other is R4'
where
R4' is
—O—$(CH_2)_m$—$S(O)_n$—R9,
—$S(O)_n$—R9,
—$S(O)_n$—$(CH_2)_m$—OH or
—$S(O)_n$—$(CH_2)_m$—O—R9,
in which
R9 is 1–4C-alkyl,
m is the number 2 or 3 and
n is the number 0, 1 or 2,
one of the substituents R5a and R5b is hydrogen and the other is hydroxyl,
R6 is hydrogen,
R7 is hydrogen and
R8 is hydrogen,
and its salts.

4. A compound I* as claimed in claim 2 in which
R1 is 1–4C-alkyl,
R2 is 1–4C-alkyl,
R3 is hydrogen,
one of the substituents R4a and R4b is hydrogen and the other is R4',
where
R4' is
—O—$(CH_2)_m$—$S(O)_n$—R9,
—$S(O)_n$—R9,
—$S(O)_n$—$(CH_2)_m$—OH or
—$S(O)_n$—$(CH_2)_m$—O—R9,
in which
R9 is 1–4C-alkyl,
m is the number 2 or 3 and
n is the number 0, 1 or 2,
one of the substituents R5a and R5b is hydrogen and the other is 1–4C-alkoxy or 1–4C-alkoxy-1–4C-alkoxy,
R6 is hydrogen,
R7 is hydrogen and
R8 is hydrogen,
and its salts.

5. A compound I* as claimed in claim 2 in which
R1 is 1–4C-alkyl,
R2 is 1–4C-alkyl,
R3 is hydrogen,
one of the substituents R4a and R4b is hydrogen and the other is R4',
where
R4' is
—O—$(CH_2)_m$—$S(O)_n$—R9,
—$S(O)_n$—R9,
—$S(O)_n$—$(CH_2)_m$—OH or
—$S(O)_n$—$(CH_2)_m$—O—R9,
in which
R9 is 1–4C-alkyl,
m is the number 2 or 3 and
n is the number 0, 1 or 2,
one of the substituents R5a and R5b is hydrogen and the other is R5',
where
R5' is
—O—$(CH_2)_q$—$S(O)_r$R10,
—$S(O)_r$—R10,
—$S(O)_r$—$(CH_2)_q$—OH or
—$S(O)_r$—$(CH_2)_q$—O—R10,
in which
R10 is 1–4C-alkyl,
q is the number 2 or 3 and
r is the number 0, 1 or 2,
R6 is hydrogen,
R7 is hydrogen and
R8 is hydrogen,
and its salts.

6. A compound I* as claimed in claim 2 in which
R1 is 1–4C-alkyl,
R2 is 1–4C-alkyl,
R3 is hydrogen,
one of the substituents R4a and R4b is hydrogen and the other is 1–4C-alkoxy or 1–4C-alkoxy-1–4C-alkoxy,
one of the substituents R5a and R5b is hydrogen and the other is R5',
where
R5' is
—O—$(CH_2)_q$—$S(O)_r$—R10,
—$S(O)_r$—R10,
—$S(O)_r$—$(CH_2)_q$—OH or
—$S(O)_r$—$(CH_2)_q$—O—R10,
in which
R10 is 1–4C-alkyl,
q is the number 2 or 3 and
r is the number 0, 1 or 2,
R6 is hydrogen,
R7 is hydrogen and
R8 is hydrogen,
and its salts.

7. A compound I* as claimed in claim 2, in which R5b is hydrogen.

8. A compound I* as claimed in claim 2 in which R5b is hydrogen and R4a is hydrogen.

9. A pharmaceutical composition comprising a compound as claimed in claim 1 and/or a pharmacologically acceptable salt thereof together with a customary pharmaceutical auxiliary and/or excipient.

10. A method of preparing a pharmaceutical composition which comprises combining a pharmaceutical auxiliary and/or excipient with a pharmacologically active compound for the prevention or treatment of a gastrointestinal disorder, or a pharmacologically acceptable salt thereof, wherein the pharmacologically active compound is a compound as claimed in claim 1.

11. A method of preventing or treating an amenable gastrointestinal disorder, which comprises administering an effective amount of a compound of claim 1 or a pharmacologically acceptable salt thereof to a subject in need of such therapy.

* * * * *